US012577599B2

(12) United States Patent
Jiang et al.

(10) Patent No.: US 12,577,599 B2
(45) Date of Patent: Mar. 17, 2026

(54) **SYNTHESIS OF HUMAN MILK OLIGOSACCHARIDES BY A BETA-N-ACETYLHEXOSAMINIDASE FROM *HALOFERULA* SP**

(71) Applicant: CHINA AGRICULTURAL UNIVERSITY, Beijing (CN)

(72) Inventors: Zhengqiang Jiang, Beijing (CN); Yihao Liu, Beijing (CN); Shaoqing Yang, Beijing (CN); Junwen Ma, Beijing (CN); Qiaojuan Yan, Beijing (CN); Ting Li, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 925 days.

(21) Appl. No.: 17/777,152

(22) PCT Filed: Oct. 20, 2020

(86) PCT No.: PCT/CN2020/122119
§ 371 (c)(1),
(2) Date: May 16, 2022

(87) PCT Pub. No.: WO2021/227363
PCT Pub. Date: Nov. 18, 2021

(65) Prior Publication Data
US 2023/0011163 A1    Jan. 12, 2023

(30) Foreign Application Priority Data
May 9, 2020    (CN) ......................... 202010386045.2

(51) Int. Cl.
*C12P 19/04*        (2006.01)
*C12N 9/24*         (2006.01)
*C12N 15/81*        (2006.01)

(52) U.S. Cl.
CPC ............ *C12P 19/04* (2013.01); *C12N 9/2402* (2013.01); *C12N 15/815* (2013.01); *C12Y 302/01052* (2013.01)

(58) Field of Classification Search
CPC ..... C12P 19/04; C12N 9/2402; C12N 15/815; C12Y 302/01052
USPC ......................................................... 514/61
See application file for complete search history.

(56)                References Cited

PUBLICATIONS

Tews et al. Bacterial chitobiase structure provides insight into catalytic mechanism and the basis of Tay-Sachs disease. Nature Structural Biology vol. 3, No. 7, p. 638-648, Jul. 1996 (Year: 1996).*
GenBank Accession: WP_052573060, family 20 glycosylhydrolase [*Haloferula* sp. BvORR071], BCT Mar. 6, 2025. (Year: 2025).*
Nyffenegger et al. Backbone structures in human milk oligosaccharides: trans-glycosylation by metagenomic β-N-acetylhexosaminidases. Appl Microbiol Biotechnol (2015) 99:7997-8009. (Year: 2015).*
Synstad et al. Expression and Characterization of Endochitinase C from Serratia marcescens BJL200 and Its Purification by a One-Step General Chitinase Purification Method. Biosci. Biotechnol. Biochem., 72 (3), 715-723, 2008. (Year: 2008).*
RID: 5Y5X7E44016; Job Title:GB|KP893201|; Program: BLASTX (conducted in Jun. 2025) (Year: 2025).*
Title: US-17-777-152-2.rge (sequence search of SEQ ID No. 2 of U.S. Appl. No. 17/777,152, conducted in Jun. 2025) (Year: 2025).*
Accession NZ_BATP01000019; Region: complement(33021 . . . 35030), *Haloferula* sp. BvORR071, whole genome shotgun sequence (retrieved in Jun. 2025) (Year: 2025).*
Visnapuu, Triinu, et al.; Identification and Characterization of a Beta-N-Acetylhexosaminidase with a Biosynthetic Activity from the Marine Bacterium Paraglaciecola hydrolytica S66T; International Journal Molecular Science; Jan. 9, 2020, vol. 21, No. 417; 22 pgs.
First Office Action issued in corresponding Chinese Application No. 202010386045.2; mailed Sep. 30, 2021, 10 pgs.
International Search Report issued corresponding International Application No. PCT/CN2020/122119; mailed Feb. 18, 2021, 10 pgs.

* cited by examiner

*Primary Examiner* — Yih-Horng Shiao
(74) *Attorney, Agent, or Firm* — HAUPTMAN HAM, LLP

(57)                ABSTRACT

The invention discloses the application of a β-N-acetyl-hexosaminidase (HaHex74) from *Haloferula* sp. in the synthesis of human milk oligosaccharides. The invention provides the use of HaHex74 protein or related biological materials thereof in any one of the following: synthesizing human milk oligosaccharides; synthesizing Lacto-N-triose II and/or Lacto-N-neotetraose; the HaHex74 protein having the amino acid sequence shown in SEQ ID No. 2 is derived from *Haloferula* sp. The β-N-acetylhexosaminidase HaHex74 disclosed by the invention possesses high-level expression, excellent hydrolysis properties and transglycosylation activity, which may make it potentially useful in the production of human milk oligosaccharides.

20 Claims, 6 Drawing Sheets

Specification includes a Sequence Listing.

Figure 1A
Figure 1B
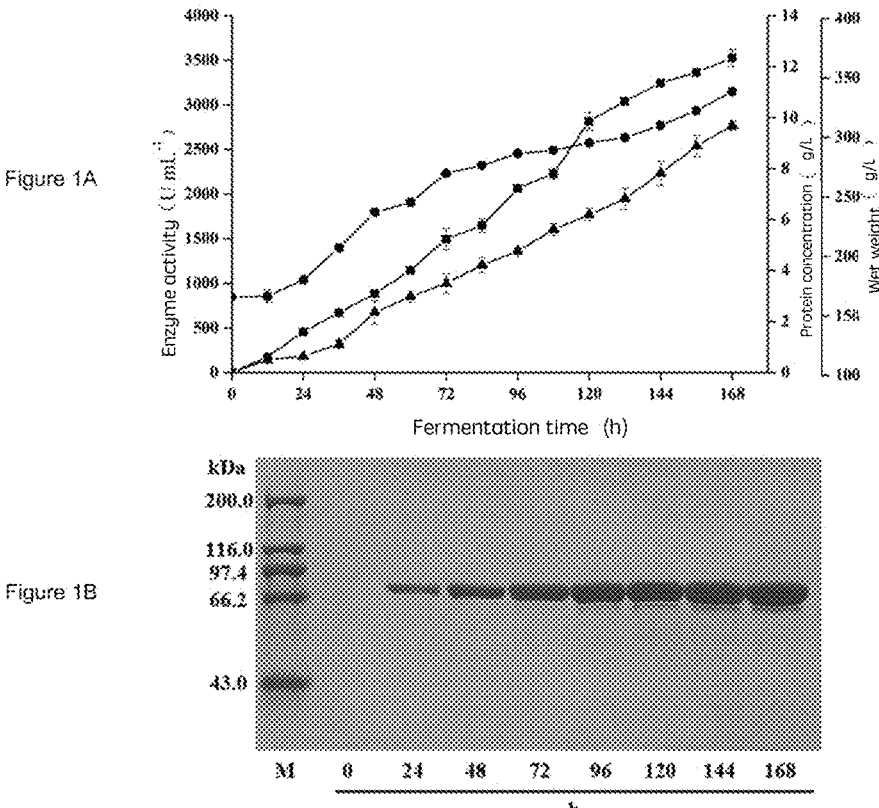
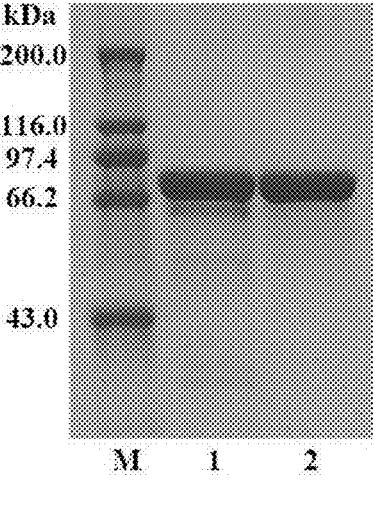
Figure 2

SEQUENCE LISTING

```
<160> NUMBER OF SEQ ID NOS: 7

<210> SEQ ID NO 1
<211> LENGTH: 491
<212> TYPE: DNA
<213> ORGANISM: Artificial sequence
<220> FEATURE:
<223> OTHER INFORMATION: Synthesized

<400> SEQUENCE: 1
atcctttttt gtagaaatgt cttggtgtcc tcgtccaatc aggtagccat ctctgaaata      60
tctggctccg ttgcaactcc gaacgacctg ctggcaacgt aaaattctcc ggggtaaaac     120
ttaaatgtgg agtaatggaa ccagaaacgt ctcttccctt ctctctcctt ccaccgcccg     180
ttaccgtccc taggaaattt tactctgctg gagagcttct tctacggccc ccttgcagca     240
atgctcttcc cagcattacg ttgcgggtaa aacggaggtc gtgtacccga cctagcagcc     300
cagggatgga aaagtcccgg ccgtcgctgg caataatagc gggcggacgc atgtcatgag     360
attattggaa accaccagaa tcgaatataa aaggcgaaca cctttcccaa ttttggtttc     420
tcctgaccca aagactttaa atttaattta tttgtcccta tttcaatcaa ttgaacaact     480
atcaaaacac a                                                         491

<210> SEQ ID NO 2
<211> LENGTH: 745
<212> TYPE: PRT
<213> ORGANISM: Artificial sequence
<220> FEATURE:
<223> OTHER INFORMATION: Synthesized

<400> SEQUENCE: 2

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Tyr Val Glu Phe Glu Pro Thr
                85                  90                  95

Ile Ile Pro Leu Pro Lys Glu Met Lys Glu Gly Gln Gly Ser Phe Pro
            100                 105                 110
```

-continued

```
Val Ser Pro Glu Thr Gly Ile Arg Tyr Asp Ala Ala Leu Asp Gly Ile
        115                 120                 125

Thr Lys Leu Phe Ala Ala Asp Leu Lys Glu Arg Thr Gly Gln Glu Pro
        130                 135                 140

Lys Thr Val Arg Glu Glu Leu Arg Ile Met Leu Pro Ser Glu Ile Arg
145                 150                 155                 160

Leu Asp Leu Asp Asn Ser Leu Asp Leu Lys Pro Gly Gly Tyr Lys Leu
                165                 170                 175

Glu Val Thr Pro Lys Gly Val Thr Val Ile Gly Lys Asp Val Ala Gly
                180                 185                 190

Ala Trp Tyr Gly Thr Arg Ser Ile Leu Gln Met Leu Pro Ala Lys Gly
        195                 200                 205

Thr Asp Ala Trp Thr Asp Lys Ala Gly Ala Pro Val Pro Val Val Ser
        210                 215                 220

Ile Thr Asp Glu Pro Arg Phe Val Trp Arg Gly Met His Leu Asp Val
225                 230                 235                 240

Gly Arg His Phe Phe Pro Ala Glu Asp Ile Lys Lys Phe Ile Asp Trp
                245                 250                 255

Leu Ala Phe His Lys Leu Asn Thr Phe His Trp His Leu Ser Glu Asp
                260                 265                 270

Gln Gly Trp Arg Ile Glu Ile Lys Lys Tyr Pro Lys Leu Thr Glu Val
        275                 280                 285

Gly Ala Phe Arg Asp Ser Ser Pro Pro Tyr Gly Asn Arg Asn Ser Asp
        290                 295                 300

Asp Gly Lys Arg Tyr Gly Gly Phe Tyr Thr Gln Glu Gln Ile Lys Asp
305                 310                 315                 320

Ile Val Ala Tyr Ala Ala Ala Arg Gln Ile Thr Ile Val Pro Glu Ile
                325                 330                 335

Asp Met Pro Gly His Met Ala Ala Ala Ile Ala Ala Tyr Pro Glu Phe
                340                 345                 350

Gly Asn Ser Asp Ile Pro Gly Tyr Ala Pro Lys Val Ile Gly Arg Trp
        355                 360                 365

Gly Val His Pro Tyr Thr Leu Ala Pro Thr Glu Glu Thr Phe Arg Phe
        370                 375                 380

Val Asp Asp Val Leu Thr Glu Leu Cys Ala Leu Phe Pro Ser Gln Tyr
385                 390                 395                 400

Ile His Ile Gly Gly Asp Glu Ala Pro Lys Asp Gln Trp Glu Lys Ser
                405                 410                 415

Pro Arg Val Lys Glu Leu Met Lys Lys Glu Gly Leu Lys Asp Gly His
                420                 425                 430

Asp Val Gln Ser Tyr Phe Ile Lys Arg Val Glu Lys Met Leu Glu Lys
        435                 440                 445

Lys Gly Arg Lys Leu Val Gly Trp Asp Glu Ile Arg Glu Gly Gly Leu
        450                 455                 460

Ser Pro Asn Ala Thr Val Met Ser Trp Arg Gly Glu Gly Gly Gly Ile
465                 470                 475                 480

Ala Ser Ala Lys Glu Gly His Asp Val Val Met Ala Ser Asn Ser His
                485                 490                 495

Leu Tyr Phe Asp His Tyr Gln Gly Val Ala Lys Asp Glu Leu Ala Lys
                500                 505                 510

Gly Glu Gln Phe Glu Ala Ile Gly Gly Phe Leu Pro Ile Ser Lys Val
        515                 520                 525

Tyr Ser Tyr Asp Pro Val Pro Lys Ala Leu Ser Pro Ala Glu Ala Lys
```

-continued

```
          530               535               540

His Val Leu Gly Val Gln Ala Gln Leu Trp Thr Glu Tyr Met Lys Asp
545               550               555               560

Trp Tyr Lys Val Glu Tyr Met Ala Phe Pro Arg Val Ala Ala Leu Ser
              565               570               575

Glu Val Ala Trp Thr Pro Val Glu Arg Lys Asp Tyr Ala Gly Phe Arg
          580               585               590

Gly Arg Leu Asp Gly Ile Leu Lys His Tyr Asp Ala Ala Gly Val Lys
          595               600               605

His Gly Asp Pro Leu Asp Pro Pro Lys Arg Glu Thr Lys Asp Gly Ser
          610               615               620

Thr Ile Thr Thr Ser Leu Gly Ala Tyr Gln Asp His Trp Pro Glu Phe
625               630               635               640

Ala Tyr Asp Gly Lys Pro Gly Thr Phe Phe Trp Ala Asp Arg Ala Leu
              645               650               655

Lys Ala Asp Asp His Val Thr Leu Lys Phe Arg Ala Ala Val Ser Gly
              660               665               670

Lys Ala Lys Val Val Thr Gly Gly Pro Ala Ser Gln Asn Gly Asp Lys
              675               680               685

Leu Ala Gly Gly Val Leu Glu Ala Ser Ser Asp Gly Ser Gln Trp Thr
          690               695               700

Gln Val Ala Glu Phe Lys Asp Gly Ser Ala Glu Gly Ala Leu Pro Ala
705               710               715               720

Gly Thr Thr Gly Leu Arg Ile Arg Val Thr Lys Pro Gln Glu Asn Trp
              725               730               735

Leu Ile Ile His Glu Ile Thr Val Glu
              740               745
```

```
<210> SEQ ID NO 3
<211> LENGTH: 2238
<212> TYPE: DNA
<213> ORGANISM: Artificial sequence
<220> FEATURE:
<223> OTHER INFORMATION: Synthesized

<400> SEQUENCE: 3
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta      240 tctctcgaga aaagagaggc tgaagcttac gtagaattcg aaccaaccat tattccattg     300
ccaaaagaga tgaaggaggg tcaaggtagt ttcccagttt ccccagagac aggtattaga     360
tatgatgctg ctttggatgg tattactaaa ttgttcgctg ctgatttgaa ggaaagaact     420
ggtcaagagc caaagactgt tagagaagag ttgagaatca tgttgccttc tgaaatcaga     480
ttggatttgg ataactcttt ggatttgaag ccaggtggtt acaaattgga ggttactcct     540
aaaggtgtta ctgttattgg taaagatgtt gctggtgctt ggtatggtac tagatctatt     600
ttgcaaatgt tgccagctaa aggtactgat gcttggactg ataaggctgg tgctccagtt     660
cctgttgttt ctatcactga tgaaccaaga ttcgtttggc gtggtatgca tttggatgtt     720
ggtagacact ttttccctgc tgaggatatt aagaagttta ttgattggtt ggctttccat     780
aaattgaaca ctttttcattg cacttgtct gaagatcaag gttggagaat tgagattaag     840
```

-continued

```
aaataccota agttgactga agttggtgct ttcagagatt cttctccacc ttatggtaac    900
agaaattctg atgatggtaa aagatacggt ggtttctaca ctcaagagca aattaaggat    960
attgttgctt acgctgctgc tagacaaatc actatcgttc cagaaatcga tatgcctggt    1020
catatggctg ctgctattgc tgcttaccca gagttcggta attctgatat tccaggttat    1080
gctcctaagg ttattggtag atggggtgtt cacccataca ctttggctcc tactgaagag    1140
acttttagat tcgttgatga tgttttgact gaattgtgtg ctttgttccc ttctcaatat    1200
attcatattg gtggagatga agctccaaag gatcaatggg agaaatctcc tagagttaag    1260
gaattgatga agaaagaggg tttgaaagat ggtcacgatg ttcaatctta cttcatcaag    1320
agagttgaaa agatgttgga gaagaaaggt agaaagttgg ttggttggga tgaaattaga    1380
gagggtggtt tgtctccaaa cgctactgtt atgtcttgga gaggtgaagg tggtggtatt    1440
gcttctgcta aagagggtca tgatgttgtt atggcttcta attctcattt gtacttcgat    1500
cactaccaag gtgttgctaa agatgaattg gctaagggtg aacaattcga ggctattggt    1560
ggtttcttgc caatttctaa ggtttactct tatgatccag ttcctaaagc tttgtctcct    1620
gctgaagcta agcacgtttt gggtgttcaa gctcaattgt ggactgaata catgaaggat    1680
tggtacaaag ttgagtatat ggctttccca agagttgctg ctttgtctga agttgcttgg    1740
actcctgttg agagaaaaga ttacgctggt tttagaggta gattggatgg tattttgaag    1800
cattacgatg ctgctggtgt taagcacgga gatccattgg atccacctaa gagagaaact    1860
aaggatggtt ctactatcac tacttctttg ggtgcttacc aagatcattg gccagagttc    1920
gcttatgatg gtaaacctgg tactttcttt tgggctgata gagctttgaa agctgatgat    1980
cacgttactt tgaagtttag agctgctgtt tctggtaaag ctaaagttgt tactggtggt    2040
ccagcttctc aaaatggaga taaattggct ggtggtgttt tggaagcttc ttctgatggt    2100
tctcaatgga ctcaagttgc tgagtttaag gatggttctg ctgagggtgc tttgcctgct    2160
ggtactactg tttgagaat cagagtcact aaaccacaag aaaactggct tattatccac    2220
gaaatcaccg ttgagtaa                                                    2238

<210> SEQ ID NO 4
<211> LENGTH: 36
<212> TYPE: DNA
<213> ORGANISM: Artificial sequence
<220> FEATURE:
<223> OTHER INFORMATION: Synthesized

<400> SEQUENCE: 4
gcagcgagct catccttttt tgtagaaatg tcttgg                                  36

<210> SEQ ID NO 5
<211> LENGTH: 34
<212> TYPE: DNA
<213> ORGANISM: Artificial sequence
<220> FEATURE:
<223> OTHER INFORMATION: Synthesized

<400> SEQUENCE: 5
cgcggatcct gtgttttgat agttgttcaa ttga                                    34

<210> SEQ ID NO 6
<211> LENGTH: 32
<212> TYPE: DNA
<213> ORGANISM: Artificial sequence
<220> FEATURE:
<223> OTHER INFORMATION: Synthesized
```

-continued

```
<400> SEQUENCE: 6
ccggaattcg aaccaaccat tattccattg cc                                    32

<210> SEQ ID NO 7
<211> LENGTH: 38
<212> TYPE: DNA
<213> ORGANISM: Artificial sequence
<220> FEATURE:
<223> OTHER INFORMATION: Synthesized

<400> SEQUENCE: 7
agaatgcggc cgcttactca acggtgattt cgtggata                              38
```

SYNTHESIS OF HUMAN MILK OLIGOSACCHARIDES BY A BETA-N-ACETYLHEXOSAMINIDASE FROM *HALOFERULA* SP

The present application is a U.S. National Phase of International Application Number PCT/CN2020/122119 filed Oct. 20, 2020, and claims priority to Chinese Application Number 202010386045.2 filed May 9, 2020.

INCORPORATION BY REFERENCE

The sequence listing provided in the file entitled Amended_SQL_C6351-055.txt, which is an ASCII text file that was created on May 11, 2022, and which comprises 11,279 bytes, is hereby incorporated by reference in its entirety:

TECHNICAL FIELD

The invention relates to the technical field of Food enzyme engineering, in particular to the use of a β-N-acetylhexosaminidase from *Haloferula* sp. in the synthesis of human milk oligosaccharides.

BACKGROUND

β-N-acetylhexosaminidases (EC 3.2.1.52) are a type of glycoside hydrolases (GHs) which catalyze the cleavage of β-linkages in N-acetylamino-β-D-hexosamines, leading to N-acetylamino-β-D-glucamine (GlcNAc) or N-acetylamino-β-D-galactosamine (GalNAc) (Chen et al. Efficient and regioselective synthesis of β-GalNAc/GlcNAc-Lactose by a bifunctional transglycosylating-N-acetylhexosaminidase from *Bifidobacterium bifidum*. Appl. Environ. Microbiol., 2016, 82, 5642-5652). Based on amino acid sequence homology, β-N-acetylhexosaminidases have been divided into GH families 3, 18, 20, 84 and 116. Recently, GH family 20 β-N-acetylhexosaminidases have been used for the synthesis of functional oligosaccharides due to their high transglycosylation activity (Liu, T., Duan, Y. W., & Yang, Q. Revisiting glycoside hydrolase family 20 β-N-acetyl-D-hexosaminidases: Crystal structures, physiological substrates and specific inhibitors. Biotechnol. Adv., 2018, 36, 1127-1138). As a class of oligosaccharides that occur naturally in human breast milk, human milk oligosaccharides (HMOs) are the third most abundant solid component in human milk after lactose and lipids (Faijes et al. Enzymatic and cell factory approaches to the production of human milk oligosaccharides. Biotechnol. Adv., 2019, 37, 667-697). Lacto-N-triose II (LNT2) and Lacto-N-neotetraose (LNnT) are the backbone structures of HMOs and have many functional activities, such as anti-inflammatory and immunomodulatory activities (Cheng et al. Human milk oligosaccharides and its acid hydrolysate LNT2 show immunomodulatory effects via TLRs in a dose and structure-dependent way. J. Funct. Foods, 2019, 59, 174-184). LNnT was approved by the Food and Drug Administration (FDA) as a new food material for Generally Recognized as Safe (GRAS) in 2015; and also approved by the European Food Safety Authority (EFSA) as a new food material in 2016, followed by marketing related products in large quantities (Bych et al. Production of HMOs using microbial hosts-from cell engineering to large scale production. Curr. Opin. Biotechnol., 2019, 56, 130-137). However, there are still challenges for the green and efficient production of LNT2 and LNnT in a large-scale.

At present, the most common methods for the synthesis of LNT2 and LNnT are whole-cell biotransformation, chemical synthesis and enzymatic synthesis. Due to the integration of metabolic mechanisms of microorganisms and the regio- and stereo-selectivities of glycosyltransferases, the whole-cell biotransformation is currently an effective means for large-scale production of HMOs (Faijes et al. Enzymatic and cell factory approaches to the production of human milk oligosaccharides. Biotechnol. Adv., 2019, 37, 667-697). LNT2 was produced by fermentation of engineered *Escherichia coli* LJ110 at a final concentration of 1.6 g $L^{-1}$ by Baumgärtner et al. (Baumgärtner et al. Synthesis of fucosylated Lacto-N-tetraose using whole-cell biotransformation. Bioorg. Med. Chem., 2015, 23, 6799-6806). β-1,3-N-acetylglucosaminyltransferase gene (LgtA) was integrated into *Escherichia coli* K12 and incubated for 44 h in a 30-L bioreactor by an optimal galactose feeding strategy, with 15.8 g/L of LNT2 by Baumgärtner et al. (Baumgärtner Florian et al., CN201580038218). LNnT was produced by fermentation of engineered *Escherichia coli* JM107 at a final concentration of 0.7 g·$L^{-1}$ by Drouillard et al. (Drouillard et al. Large-scale synthesis of H-antigen oligosaccharides by expressing *Helicobacter pylori* a-1,2-fucosyltransferase in metabolically engineered *Escherichia coli* cells. Angew. Chem., Int. Ed., 2006, 45, 1778-1780). In addition, some scholars have studied the biosynthesis of LNnT by *Bacillus subtilis* as chassis cells. For example, Liu et al. (Liu Long et al., CN201910146431) integrated two β-1.4-galactosyltransferase genes on the genome of *Bacillus subtilis* 168 ΔamyE: P43-lacY, P43-lgtB. PxylA-comK, and expressed β1,3-N-glucosaminyltransferase gene exogenously to obtain a recombinant *Bacillus subtilis* 168, which was incubated for 48 h under the optimal glucose feeding strategy, with 1.3 g/L of LNnT. Dong et al. (Dong et al. Modular pathway engineering of key precursor supply pathways for Lacto-N-ncotetraose production in *Bacillus subtilis*. Biotechnol. Biofuels, 2019, 12, 212) produced LNnT by fermentation of engineered *B. subtilis* 168 at a final concentration of 4.5 g $L^{-1}$. As the primary means of large-scale production of LNT2 and LNnT, the production cost of whole-cell biotransformation remains high because of the low yield and the need to modify the metabolic pathways of chassis cells at the early stage, and to optimize the fermentation process at the later stage.

The chemical synthesis of LNT2 and LNnT requires many steps to prevent side reactions, resulting in low synthesis efficiency and not suitable for large-scale production (Faijes et al. Enzymatic and cell factory approaches to the production of human milk oligosaccharides. Biotechnol. Adv., 2019, 37, 667-697). Compared with the chemical synthesis, enzymatic synthesis has become an effective approach for the synthesis of HMOs due to its good stereo- and regio-selectivities, environmental friendliness, and capability of effectively guaranteeing specific glycosidic bond configurations. However, the enzymatic synthesis of LNT2 and LNnT mainly depends on activated artificial donors, such as p-nitrophenyl-β-N-acetylglucosaminide (pNP-GlcNAc) and uridine diphosphate-N-acetylglucosamine (UDP-GlcNAc). Activated artificial donors are not suitable for the efficient synthesis of food-grade LNT2 and LNnT because of their high cost and safety issues (Nyffenegger et al. Backbone structures in human milk oligosaccharides: trans-glycosylation by metagenomic β-N-acetyl-hexosaminidases. Appl. Microbiol. Biotechnol., 2015, 99, 7997-8009). Chitin, the second most abundant natural polymer, after cellulose, is a linear polysaccharide of GlcNAc linked by β-1,4-glycosidic bonds (Lv et al. Highly efficient and selective biocatalytic production of glucosamine from chitin. Green Chem., 2017, 19, 527-535). The degradation products of chitin, N-acetyl chitooligosaccharides might serve as natural GlcNAc donors for the synthesis of LNT2 (Nyffenegger et al. Backbone structures in human milk oligosaccharides: trans-glycosylation by metagenomic β-N-acetylhexosaminidases. Appl. Microbiol. Biotechnol., 2015, 99, 7997-8009). Therefore, there are broad market prospects from the conversion of chitin to LNT2 using β-N-acetyl-hexosaminidase and chitinase, and further in the synthesis of high value-added LNnT by β-galactosidase.

β-N-acetylhexosaminidases have been mainly used for biological control (Li Daqi et al., CN 201210356675), feed addition (Zhou Zhigang et al., CN201210065384) and N-acetyl chitooligosaccharides production (Jiang Zhengqiang et al., CN 201811105536). At present, there is no patent and literature report on the conversion of chitin to LNT2 using β-N-acetylhexosaminidase and chitinase, and further the synthesis of LNnT using the β-galactosidase. There are relatively few reports on the synthesis of LNT2 and LNnT using β-N-acetylhexosaminidases and β-galacto-sidases in the world. Nyfenegger et al. (Nyffenegger et al. Backbone structures in human milk oligosaccharides: trans-glycosylation by metagenomic β-N-acetylhexosaminidases. Appl. Microbiol. Biotechnol., 2015, 99:7997-8009) obtained two β-N-acetylglucosaminidases (HEX1 and HEX2) from a soil-derived metagenomic library and suc-cessfully expressed in *E. coli*, which were reacted with N-acetyl chitobiose and lactose at 25° C. for 2 h with the LNT2 conversion ratios of 2% and 8%, respectively. Zeuner et al. (Zeuner et al. Thermostable β-galactosidases for the synthesis of human milk oligosaccharides. New Biotechnol., 2016, 33, 355-360) used three thermophilic β-galactosidases to synthesize LNnT with lactose and LNT2 as glycoside donors and acceptors, respectively, with low yields of 7.1%, 5.2%, and 1.0%, respectively. *Haloferula* sp. belongs to subdivision 1 of the phylum Verrucomicrobia (Bibi et al. *Haloferula luteola* sp nov., an endophytic bacterium isolated from the root of a halophyte, *Rosa rugosa*, and emended description of the genus *Haloferula*. Int. J. Syst. Evol. Microbiol., 2011, 61, 1837-1841), there are few reports on this genus, and there is no report on β-N-acetylhexosamini-dases from *Haloferula* sp. currently.

SUMMARY

The present invention aims to provide synthesis of human milk oligosaccharides by a β-N-acetylhexosaminidase from *Haloferula* sp. (HaHex74).

In the first aspect, the present invention claims use of a HaHex74 protein or related biological material thereof in any one of the following;
- (a1) synthesis of human milk oligosaccharides; and
- (a2) synthesis of Lacto-N-triose II and/or Lacto-N-neo-tetraose.

The HaHex74 protein is derived from *Haloferula* sp., and specifically may be any one of the following;
- (A1) a protein comprising an amino acid sequence at positions 94-745 of SEQ ID No.2 or shown in SEQ ID No.2;
- (A2) a protein comprising an amino acid sequence includ-ing substitution and/or deletion and/or addition of one or several amino acid residues in the amino acid sequence at positions 94-745 of SEQ ID No.2 or shown in SEQ ID No.2 and having the same function;
- (A3) a protein having 99% or more, 95% or more, 90% or more, 85% or more or 80% or more homology with the amino acid sequence defined in any one of (A1)-(A2) and having the same function; and
- (A4) a fusion protein obtained by attaching a tag to the N-terminus and/or the C-terminus of the protein defined in any one of (A1)-(A3).

The relevant biological material may be a nucleic acid molecule capable of expressing the HaHex74 protein or an expression cassette, recombinant vector, recombinant bac-teria or transgenic cell line containing the nucleic acid molecule.

The tag in the above-mentioned proteins refers to a polypeptide or a protein expressed by fusion with a protein of interest using DNA in vitro recombination technology to facilitate expression, detection, tracing and/or purification of the protein of interest. The tag may be a Flag tag, a His tag, an MBP tag, an HA tag, a myc tag, a GST tag, and/or a SUMO tag.

In the above-mentioned proteins, homology refers to the identity of amino acid sequences. The identity of amino acid sequence can be determined using homology search sites on the Internet, such as the BLAST webpage of the NCBI homepage. For example, the identity of a pair of amino acid sequences may be searched and calculated to generate the identity value (%) in advanced BLAST2.1, by setting the Expect value to 10 and all Filters to OFF in the blastp program, and setting Gap existence cost, Per residue gap cost and Lambda ratio to 11, 1 and 0.85 (default values) respectively in BLOSUM62 Matrix.

In the above-mentioned proteins, more than 95% homol-ogy may be at least 96%, 97%, and 98% identity. More than 90% homology may be at least 91%, 92%, 93%, and 94% identity. More than 85% homology may be at least 86%, 87%, 88%, and 89% identity. More than 80% homology may be at least 81%, 82%, 83%, and 84% identity. In the second aspect, the present invention claims a method for the syn-thesis of Lacto-N-triose II.

The method for the synthesis of Lacto-N-triose II as claimed in the invention may comprise the following steps (b1) or (b2) or (b3);
- (b1) synthesizing Lacto-N-triose II (LNT2) from chitin hydrolysate and β-lactose under the catalysis of a HaHex74 protein as a biological enzyme;
- (b2) performing chitin hydrolysis catalyzed by a chitinase to obtain the chitin hydrolysate; then synthesizing Lacto-N-triose II (LNT2) from the chitin hydrolysate and β-lactose under the catalysis of a HaHex74 protein; and (b3) synthesizing Lacto-N-triose II (LNT2) from the chitin hydrolysate and β-lactose under the catalysis of a chitinase and a HaHex74 protein as biological enzymes.

The HaHex74 protein is a protein as described in any one of (A1) to (A4).

In the third aspect, the present invention claims a method for the synthesis of Lacto-N-neotetraose (LNnT).

The method for the synthesis of Lacto-N-neotetraose (LNnT) as claimed in the invention may comprise the following steps (c1) or (c2);
- (c1) preparing Lacto-N-triose II (LNT2) according to the method of the second aspect; then synthesizing Lacto-N-neotetraose (LNnT) from Lacto-N-triose II (LNT2) and β-lactose under the catalysis of a β-galactosidase; and
- (c2) synthesizing Lacto-N-triose II (LNT2) and Lacto-N-neotetraose (LNnT) from chitin and β-lactose under the catalysis of a chitinase, a HaHex74 protein and a β-galactosidase as biological enzymes.

The HaHex74 protein is a protein as described in any one of (A1) to (A4).

Furthermore, in the (b1) and the (b2), the chitin hydrolysate is a mixture of chitobiose and N-acetylglucosamine.

Furthermore, Lacto-N-triose II (LNT2) is synthesized from chitin hydrolysate and β-lactose catalyzed by the HaHex74 protein as a biological enzyme under conditions of pH 7.5, and/or a temperature of 40° C., and/or a content of β-lactose in the reaction system of 0.8 M; and/or a content of the HaHex74 protein in the reaction system of 3-5 U/mL (such as 4 U/mL), and/or a reaction time of 10 h.

Furthermore, chitin hydrolysate is obtained from the hydrolysis of chitin catalyzed by the chitinase under conditions of pH 5.5, and/or a temperature of 55° C., and/or a content of the chitinase in a reaction system of 5 U/mL, and/or a reaction time of 24 h.

Furthermore, Lacto-N-neotetraose (LNnT) is synthesized from Lacto-N-triose II (LNT2) and β-lactose catalyzed by a β-galactosidase under conditions of natural pH (pH 7.0), and/or a temperature of 50° C., and/or a content of β-galactosidase in the reaction system of 0.1 U/mL, and/or a reaction time of 10 h.

In each of the above aspects, the HaHex74 protein shows an optimum pH of 6.5 and an optimum temperature of 45° C.

In each of the above aspects, the HaHex74 protein may be prepared according to a method comprising the steps of introducing a nucleic acid molecule encoding the HaHex74 protein into a yeast receptor to obtain recombinant yeast: performing fermentation culture on the recombinant yeast according to the following steps to obtain the HaHex74 protein from a fermentation product;

(d1) a basic culture stage: inoculating the recombinant yeast into BSM medium supplemented with 50 g/L glycerol for culture, adjusting a temperature to 30° C. and pH to 4.0, and starting the glycerol fed-batch culture stage when the glycerol concentration is below 10 g/L.

(d2) a glycerol fed-batch culture stage: feeding 500 g/L glycerol, maintaining the glycerol concentration at 10-25 g/L, adjusting a temperature to 28° C., pH to 5.0, and the dissolved oxygen content to 10-20% until the end of fermentation.

In (d1), the step of adding PTM1 to the fermentation system is also included. The PTM1 is added in an amount of 4.35 mL/L starting broth.

In (d1), the recombinant yeast is inoculated in an amount of 10% by volume.

In (d1), the rotation speed is controlled to be 600 rpm during culture: in (d2), the rotation speed is controlled at 800 rpm while culturing.

Before (d1), a seed culture stage may also be included: inoculating the recombinant yeast into BMGY medium and culturing is to $OD_{600}$ of about 10.0 at 30° C. In the seed culture stage, a rotation speed is controlled at 200 rpm. Furthermore, the HaHex74 protein from the fermentation product may be performed according to a process comprising the steps of centrifuging the fermentation product to collect supernatant: dialyzing the supernatant in a Tris-HCl buffer solution, and centrifuging to obtain crude liquor: purifying the crude liquor using an agarose weak anion exchange column DE52 to obtain the HaHex74 protein.

Furthermore, the DE52 affinity column is equilibrated with buffer A for 5-10 column volumes, the collected crude enzyme is loaded at a flow rate of 0.5 mL/min, and eluted linearly with buffer A and buffer B to an $OD_{280}$<0.05, fractions with β-N-acetylhexosaminidase activity are collected and dialyzed to obtain the purified product as the HaHex74 protein.

Wherein buffer A is a buffer solution containing 20 mM Tris-HCl (pH 8.0); buffer B is a 20 mM Tris-HCl buffer solution (pH 8.0) containing NaCl (500 mM).

Furthermore, the nucleic acid molecule encoding the HaHex74 protein may be a DNA molecule as described in any one of the following;

(B1) a DNA molecule represented by positions 280-2238 of SEQ ID No. 3 or SEQ ID No. 3;

(B2) a DNA molecule hybridizing with the DNA molecule defined by b1) or b2) under stringent conditions and encoding the HaHex74 protein;

(B3) a DNA molecule having 99% or more, 95% or more, 90% or more, 85% or more or 80% or more homology with the DNA sequence defined by (B1) or (B2) and encoding the HaHex74 protein.

In the above genes, the stringent conditions may be as follows: hybridizing in a mixed solution of 7% sodium dodecyl sulfate (SDS), 0.5 M $Na_3PO_4$ and 1 mM EDTA at 50° C., and rinsing in 2×SSC, 0.1% SDS at 50° C.; it can also be: hybridizing in a mixed solution of 7% SDS, 0.5 M $Na_3PO_4$ and 1 mM EDTA at 50° C., and rinsing in 1×SSC, 0.1% SDS at 50° C.; it can also be: hybridizing in a mixed solution of 7% SDS, 0.5 M $Na_3PO_4$ and 1 mM EDTA at 50° C., and rinsing in 0.5×SSC, 0.1% SDS at 50° C.; it can also be: hybridizing in a mixed solution of 7% SDS, 0.5 M $Na_3PO_4$ and 1 mM EDTA at 50° C., and rinsing in 0.1×SSC, 0.1% SDS at 50° C.; it can also be: hybridizing in a mixed solution of 7% SDS, 0.5 M $Na_3PO_4$ and 1 mM EDTA at 50° C., and rinsing in 0.1×SSC, 0.1% SDS at 65° C.; it can also be: hybridizing in a solution of 6×SSC, 0.5% SDS at 65° C. and washing membranes once each with 2×SSC, 0.1% SDS and 1×SSC, 0.1% SDS.

In the above nucleic acid molecules, homology refers to the identity of nucleotide sequences. The identity of nucleotide acid sequences can be determined using homology search sites on the Internet, such as the BLAST webpage of the NCBI homepage. For example, the identity of a pair of nucleotide acid sequences may be searched and calculated to generate the identity value (%) in advanced BLAST2.1, by setting the Expect value to 10 and all Filters to OFF in the blastp program, and setting Gap existence cost, Per residue gap cost and Lambda ratio to 11, 1 and 0.85 (default values) respectively in BLOSUM62 Matrix.

In the above nucleic acid molecules, more than 95% homology may be at least 96%, 97% and 98% identity. More than 90% homology may be at least 91%, 92%, 93%, and 94% identity. More than 85% homology may be at least 86%, 87%, 88%, and 89% identity. More than 80% homology may be at least 81%, 82%, 83%, and 84% identity. Furthermore, the nucleic acid molecule may be introduced into the yeast receptor in the form of a recombinant vector.

The promoter in the recombinant vector that initiates transcription of the nucleic acid molecule may be a GAP promoter.

Furthermore, the recombinant vector is a recombinant vector obtained after cloning the nucleic acid molecule into a pGAP9K vector (e.g., between EcoR I and Not I). Wherein the pGAP9K vector is a plasmid obtained by replacing an AOX1 promoter in a pPIC9K vector with a GAP promoter.

The sequence of the GAP promoter is shown in SEQ ID No.1.

Furthermore, the yeast is *Pichia pastoris*.

Furthermore, the *Pichia pastoris* is *Pichia pastoris* GS115.

In the fourth aspect, the present invention claims a process for the preparation of the HaHex74 protein as hereinbefore described.

The preparation method of HaHex74 protein may comprise the following steps: introducing a nucleic acid molecule encoding the HaHex74 protein into a yeast receptor to obtain recombinant yeast: performing fermentation culture on the recombinant yeast according to the following steps to obtain the HaHex74 protein from a fermentation product;

(d1) a basic culture stage: inoculating the recombinant yeast into BSM medium supplemented with 50 g/L glycerol for culture, adjusting the temperature to 30° C. and pH to 4.0, and starting the glycerol fed-batch culture stage when the glycerol concentration is below 10 g/L.

(d2) a glycerol fed-batch culture stage: feeding 500 g/L glycerol, maintaining the glycerol concentration at 10-25 g/L, adjusting a temperature to 28° C., pH to 5.0, and the dissolved oxygen content to 10-20% until the end of fermentation.

In (d1), the step of adding PTM1 to the fermentation system is also included. The PTM1 is added in an amount of 4.35 mL/L starting broth.

In (d1), the recombinant yeast is inoculated in an amount of 10% by volume.

In (d1), the rotation speed is controlled to be 600 rpm during culture: in (d2), the rotation speed is controlled at 800 rpm while culturing.

Before (d1), a seed culture stage may also be included: inoculating the recombinant yeast into BMGY medium and culturing at 30° C. to $OD_{600}$ of about 10.0. In the seed culture stage, a rotation speed is controlled at 200 rpm.

Furthermore, the HaHex74 protein from the fermentation product may be performed according to a process comprising the steps of centrifuging the fermentation product to collect supernatant: dialyzing the supernatant in a Tris-HCl buffer solution, and centrifuging to obtain crude liquor: purifying the crude liquor using an agarose weak anion exchange column DE52 to obtain the HaHex74 protein.

Furthermore, the DE52 affinity column is equilibrated with buffer A for 5-10 column volumes, the collected crude liquor is loaded at a flow rate of 0.5 mL/min, and eluted linearly with buffer A and buffer B to an $OD_{280}$<0.05, fractions with β-N-acetylhexosaminidase activity are collected and dialyzed to obtain the purified product as the HaHex74 protein.

Wherein buffer A is a buffer solution containing 20 mM Tris-HCl (pH 8.0); buffer B is a 20 mM Tris-HCl buffer solution (pH 8.0) containing NaCl (500 mM).

Furthermore, the nucleic acid molecule encoding the HaHex74 protein may be a DNA molecule as described in any one of the following;

(B1) a DNA molecule represented by positions 280-2238 of SEQ ID No. 3 or SEQ ID No. 3;

(B2) a DNA molecule hybridizing with the DNA molecule defined by b1) or b2) under stringent conditions and encoding the HaHex74 protein;

(B3) a DNA molecule having 99% or more, 95% or more, 90% or more, 85% or more or 80% or more homology with the DNA sequence defined by (B1) or (B2) and encoding the HaHex74 protein.

In the above genes, the stringent conditions may be as follows: hybridizing in a mixed solution of 7% sodium dodecyl sulfate (SDS), 0.5 M $Na_3PO_4$ and 1 mM EDTA at 50° C., and rinsing in 2×SSC, 0.1% SDS at 50° C.; it can also be: hybridizing in a mixed solution of 7% SDS, 0.5 M $Na_3PO_4$ and 1 mM EDTA at 50° C., and rinsing in 1×SSC.

0.1% SDS at 50° C.; it can also be: hybridizing in a mixed solution of 7% SDS, 0.5 M $Na_3PO_4$ and 1 mM EDTA at 50° C., and rinsing in 0.5×SSC, 0.1% SDS at 50° C.; it can also be: hybridizing in a mixed solution of 7% SDS, 0.5 M $Na_3PO_4$ and 1 mM EDTA at 50° C., and rinsing in 0.1×SSC, 0.1% SDS at 50° C.; it can also be: hybridizing in a mixed solution of 7% SDS, 0.5 M $Na_3PO_4$ and 1 mM EDTA at 50° C., and rinsing in 0.1×SSC, 0.1% SDS at 65° C.; it can also be: hybridizing in a solution of 6×SSC, 0.5% SDS at 65° C. and washing membranes once each with 2×SSC, 0.1% SDS and 1×SSC, 0.1% SDS.

In the above nucleic acid molecules, homology refers to the identity of nucleotide sequences. The identity of the nucleotide acid sequence can be determined using homology search sites on the Internet, such as the BLAST webpage of the NCBI homepage. For example, the identity of a pair of nucleotide acid sequences may be searched and calculated to generate the identity value (%) in advanced BLAST2.1, by setting the Expect value to 10 and all Filters to OFF in the blastp program, and setting Gap existence cost, Per residue gap cost and Lambda ratio to 11, 1 and 0.85 (default values) respectively in BLOSUM62 Matrix.

In the above nucleic acid molecules, more than 95% homology may be at least 96%, 97%, and 98% identity. More than 90% homology may be at least 91%, 92%, 93%, and 94% identity. More than 85% homology may be at least 86%, 87%, 88%, and 89% identity. More than 80% homology may be at least 81%, 82%, 83%, and 84% identity. Furthermore, the nucleic acid molecule may be introduced into the yeast receptor in the form of a recombinant vector.

The promoter in the recombinant vector that initiates transcription of the nucleic acid molecule may be a GAP promoter.

Furthermore, the recombinant vector is a recombinant vector obtained after cloning the nucleic acid molecule into a pGAP9K vector (e.g., between EcoR I and Not I). Wherein the pGAP9K vector is a plasmid obtained by replacing an AOX1 promoter in a pPIC9K vector with a GAP promoter.

The sequence of the GAP promoter is shown in SEQ ID No.1.

Furthermore, the yeast is *Pichia pastoris*.

Furthermore, the *Pichia pastoris* is *Pichia pastoris* GS115.

BRIEF DESCRIPTION OF DRAWINGS

FIGS. 1A and 1B Time course of HaHex74 expressed in *P. pastoris* (1 A) and SDS-PAGE analysis of extracellular proteins (1B). ((■): enzyme activity: (▲): protein concentration: (●): wet weight).

FIG. 2 SDS-PAGE analysis of HaHex74 before and after purification.

EMBODIMENTS

Figures 3A, 3B, 3C, 3D:
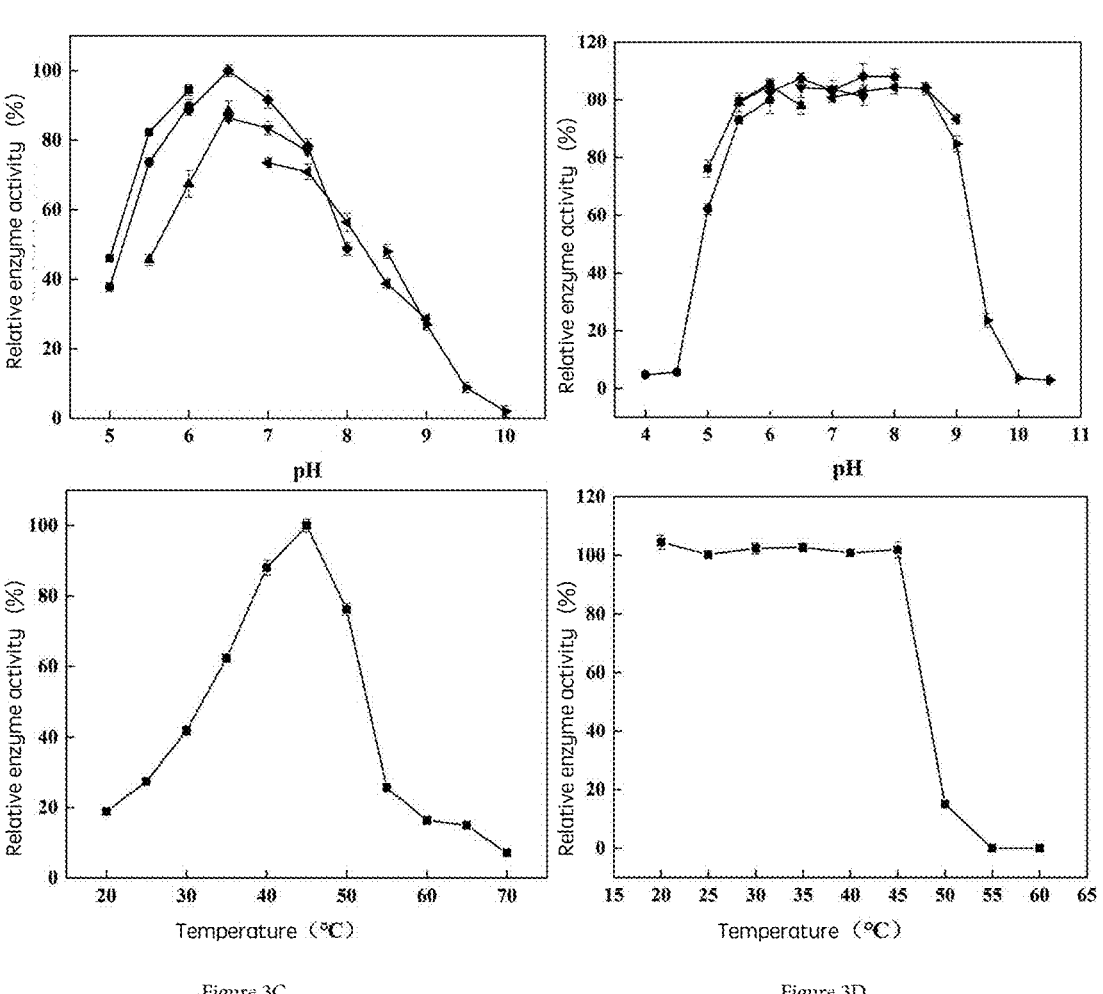
FIGS. 3A-3D Optimal pH (3A), pH stability (3B), optimal temperature (3C) and thermostability (3D) of HaHex74. Wherein, (■) citric acid buffer (pH 5.0-6.0), (●) acetic acid-sodium acetate buffer (pH 4.0-6.0), (▲) MES buffer (pH 5.5-6.5), (▼) MOPS buffer (pH 6.5-7.5), (◆) phosphate buffer (pH 6.0-8.0), (◄) Tris-HCl buffer (pH 7.0-9.0), (►) glycine-sodium hydroxide buffer (pH 8.5-10.5).

The following examples facilitate a better understanding of the present invention but do not limit the present invention. The experimental methods in the following examples are conventional unless otherwise specified. The experimental materials used in the following examples were purchased from conventional biochemical reagent stores unless otherwise specified. In the quantitative experiments of the following examples, triplicate experiments are set up, and the results are averaged.

The enzyme activity of β-N-acetylhexosaminidase in the following examples was determined as follows:

0.1 mL of appropriately diluted enzyme solution was added to 0.1 mL of a 2 mM pNP-GlcNAc substrate solution (prepared in 50 mM phosphate buffer, pH 6.5), and the mixture was reacted at 45° C. for 10 min to determine the absorbance at 410 nm ($OD_{410}$) (Yang et al. Biochemical characterization of the first fungal glycoside hydrolyase family 3 β-N-acetylglucosaminidase from *Rhizomucor miehei*. J. Agric. Food Chem., 2014, 62, 5181-5190). A standard enzyme-activity unit of β-N-acetylhexosaminidase is given below: one unit (1 U) is the amount of enzyme required to produce 1 μmol of pNP per minute under the above reaction conditions.

Specific enzyme activity is defined as the unit of enzyme activity per 1 mg of protein, expressed as $U \cdot mg^{-1}$. One unit of β-N-acetylhexosaminidase activity is defined as: under the conditions of pH 6.5, 45° C., the amount of enzyme required to release 1 μmol of pNP per minute by decomposing 2 mM pNP-GlcNAc substrate solution (formulated in 50 mM phosphate buffer, pH 6.5) and is calculated as follows: H=Cx×n/(T×V), wherein H represents the enzyme activity (U/mL), Cx represents the amount of pNP produced (μmol), n represents the dilution multiple of the enzyme solution, T represents the reaction time (min), and V represents the volume of enzyme solution (mL) after addition of the dilution.

Example 1. Identification of β-N-Acetylhexosaminidase Gene and Construction of Engineered *P. pastoris* GS115

1. Identification of β-N-Acetylhexosaminidase Gene

The reported protein sequence of β-N-acetylhexosaminidase was searched by CAZy database, and the homologous sequence alignment analysis was performed to obtain a GH family 20 β-N-acetylhexosaminidase gene (named HaHex74) from *Haloferula* sp. The nucleotide sequence of the HaHex74 gene is "ATG+ positions 280-2238 of SEQ ID No.3", and encodes the amino acid sequence shown as "Met+ positions 94-745 of SEQ ID No.2". HaHex74 shared the highest (61%) homology with a soil metagenomic β-N-acetylhexosaminidase (AKC34129). The gene was synthesized by Sangon Biotech (Shanghai) Co., Ltd.

2. Construction of Engineered *P. pastoris* GS115 for the β-N-Acetylhexosaminidase Expression 2.1 Primers were Designed According to a Glyceraldehyde-3-Phosphate Dehydrogenase (GAP) Promoter Gene Sequence in the *Pichia pastoris* GS115 Genome:

```
GAP1:
5'-GCAGCGAGCTCATCCTTTTTTGTAGAAATGTCTTGG-3'; (SEQ ID NO: 4)

GAP2:
5'-CGCGGATCCTGTGTTTTGATAGTTGTTCAATTGA-3'. (SEQ ID NO: 5)
```

The GAP promoter was amplified from the *Pichia pastoris* GS115 genome. The GAP promoter fragment and pPIC9K vector were subjected to double digestion with Sac I and BamHI and ligated by T4 DNA ligase to obtain the modified expression vector, named pGAP9K. That is, the AOX1 promoter in the pPIC9K vector was replaced with the GAP promoter. Wherein, the GAP promoter sequence is shown in SEQ ID No.1.

2.2 Expression Primers were Designed According to the Sequence of β-N-Acetylhexosaminidase, EcoRI and NotI Restriction Sites were Respectively Added to the Following Upstream Primer and the Downstream Primer:

```
Upstream primer:
5'-CCGGAATTCGAACCAACCATTATTCCATTGCC-3'; (SEQ ID NO: 6)

Downstream primer:
5'-AGAATGCGGCCGCTTACTCAACGGTGATTTCGTGGATA-3'. (SEQ ID NO: 7)
```

The PCR amplification was performed with the above primers, and the conditions were as follows: 95° C. for 30 s; 95° C. for 20 s, 58° C. for 20 s, 72° C. for 1 min followed by 34 cycles; and final extension at 72° C. for 5 min. PCR products were recovered by 1% agarose gel electrophoresis and subjected to double digestion with EcoRI and NotI. The double restriction enzyme digested products were ligated with a vector backbone fragment of a yeast expression vector pGAP9K which was subjected to the same double digestion by T4 DNA ligase, and was then transformed into *Escherichia coli* DH5a. The recombinant expression vector verified by sequencing was designated as pGAP9K-Ha-Hex74. The obtained recombinant *P. pastoris* expression vector pGAP9K-HaHex74 was subjected to linearization by a restriction endonuclease XbaI, and transformed into *P.*

*pastoris* GS115 by electroporation. The GAP promoter sequence in the recombinant expression vector pGAP9K-HaHex74 is the DNA molecule in SEQ ID No.1 (i.e. constructing a new expression vector pGAP9K by replacing the AOX1 promoter in the pPIC9K vector with the GAP promoter through double digestion with Sac I and BamH I); the complete ORF sequence of the recombinant expression vector pGAP9K-HaHex74 is a DNA molecule in SEQ ID No.3, wherein positions 1-279 are sequences on the pGAP9K vector, and positions 280-2238 are HaHex74 gene sequences.

Example 2 Preparation of the β-N-Acetylhexosaminidase (HaHex74) and its Enzymatic Properties 1. Expression of the β-N-Acetylhexosaminidase in *P. pastoris* GS115

The recombinant strains obtained in Example 1 were spread on MD plates (1.34% YNB, $4 \times 10^{-5}$% biotin, 2% glucose), $His^+$ transformants obtained from MD plates were scraped with sterile water, and 100 μL of transformants was spread on YPD-G418 plates (1% yeast extract, 2% tryptone, 2% glucose, G418 concentrations of 2, 3, 4, 6 mg/mL, respectively) at different concentrations. After incubation for 3-5 d at 30° C., transformants were picked out and cultured in BMGY medium for 16-18 h, followed by centrifuging at 3000 rpm for 5 min. Cells were collected, then resuspended with the BMGY medium until the $OD_{600}$ was about 1.0, and glycerol was fed in batches to express the target protein. The above mixture was cultured in 20 mL medium in a 100 mL triangular flask at 30° C. and 200 rpm. Glycerol was added every 24 h to a final concentration of 1% for 3 d, the enzyme activity of the fermentation broth was determined, and the expression of HaHex74 recombinant protein was analyzed by SDS-PAGE.

2. High Cell Density Fermentation

The strain with the highest enzyme activity obtained in step 1 of Example 2 was subjected to high-density fermentation in a 5-L fermenter. The medium used during the fermentation (seed medium BMGY, fermentation minimal medium BSM and glycerol fed-batch medium) was performed according to *Pichia* Fermentation Process Guidelines (Version B, 053002, Invitrogen). The whole fermentation process adopted two stages of basic culture and glycerol fed-batch culture.

(1) Seed culture; the strain with the highest enzyme activity in flask shaking fermentation was inoculated into 150 mL BMGY medium and cultured at 30° C. and 200 rpm until the $OD_{600}$ was about 10.0.

(2) Basic culture; the seed solution obtained in step (1) was inoculated into a 5-L fermenter (containing 1.35 L of a fermentation basic medium BSM and 5% (50 g/L) of glycerol, the fermenter was sterilized, the pH was adjusted to 4.0 by 28% concentrated ammonia water, and an initial fermentation broth with 4.35 mL/L of PTM1 (trace elements known in the art for promoting yeast expression) was added, with an inoculum volume of 10% (v/v), a rotation speed of 600 rpm, and a temperature of 30° C. When the glycerol concentration was below 1% (10 g/L), 50% (w/v) glycerol (500 g/L) feed medium was fed in batches.

(3) Fed-batch culture with glycerol: 50% (w/v) glycerol (500 g/L) was fed in batches under conditions of 28° C., pH 5.0, and a rotation speed of 800 rpm, a glycerol concentration was maintained at 1%-2.5% (10 g/L$^{-25}$ g/L), the dissolved oxygen was constantly monitored, and the rotation speed and the ventilation volume were timely adjusted to maintain the DO at 10%-20% until the fermentation end-point.

The wet weight, protein content and enzyme activity were determined during fermentation. The results showed that the highest enzyme activity and protein concentration were 3500 U/mL and 9.7 g/L, respectively after 168-h fermentation (FIGS. 1A and 1B).

3. Purification of β-N-Acetylhexosaminidase

After the high-density fermentation, the fermentation broth was centrifuged at 10,000 g for 5 min, the supernatant was collected, and 50 mL of the supernatant was dialyzed in Tris-HCl buffer solution (20 mM, pH 8.0) overnight. The dialysate was centrifuged at 10,000 g for 5 min to obtain a crude enzyme solution. The crude enzyme solution was purified by a (diethylamino) ethyl DE52 column (DEAE Sepharose Fast Flow) to obtain purified HaHex74.

Specific Steps were as Follows:

The DE52 column was equilibrated with Buffer A for 5-10 column volumes, the collected enzyme solution was loaded at a flow rate of 0.5 mL/min. Buffer A was eluted linearly with Buffer B to an OD 280<0.05 using a protein purification system (ÄKTA, GE Healthcare, USA) (elution procedure: 0-30 min, A 100%: 30-120 min, A 100%-0, B 0-100%: 120-135 min, B 100%: % denotes volume percent). Fractions with β-N-acetylhexosaminidase activity were collected, checked for purity by SDS-PAGE, and dialyzed to obtain purified product.

Wherein buffer A was a buffer solution containing 20 mM Tris-HCl (pH 8.0); buffer B was 20 mM Tris-HCl buffer (pH 8.0) containing NaCl (500 mM).

The purified product obtained from the crude enzyme solution of recombinant strain was the recombinant protein HaHex74.

The SDS-PAGE of the crude enzyme solution of and the resulting purified product (recombinant protein HaHex74) were shown in FIG. 2, in which lane M represented a molecular weight protein standard, lane 1 represented the recombinant protein HaHex74 crude enzyme, and lane 2 represented the HaHex74 pure enzyme. FIG. 2 showed that the molecular weight of the recombinant protein HaHex74 was approximately 74 kDa, consistent with the expected size. The enzyme activity of β-N-acetylhexosaminidase was detected, with the crude enzyme solution and the purified enzyme solution as enzyme solutions to be detected respectively, and the corresponding inactivated protein as a control. The total enzyme activity of the crude enzyme solution shown in Table 1 was 3500 U, and the specific enzyme activity was 360.8 U $mg^{-1}$; the total enzyme activity of purified enzyme solution was 2890 U, and its specific enzyme activity was 385.3 U $mg^{-1}$; the purification fold was 1.1.

TABLE 1

Purification of β-N-acetylhexosaminidase HaHex74

| Purification Step | Total enzyme activity (U) | Total Protein | Specific enzyme activity (U mg$^{-1}$) | Purification fold | Recovery rate (%) |
|---|---|---|---|---|---|
| Crude enzyme solution | 3500 | 9.7 | 360.8 | 1 | 100 |
| DE52 | 2890 | 7.5 | 385.3 | 1.1 | 82.6 |

4. Enzymatic Properties of β-N-Acetylhexosaminidase (1) Determination of Optimal pH The purified HaHex74 was used to be detected, and enzyme activity was determined under 40° C. in different buffer solution systems respectively, and the relative enzyme activity was calculated by taking the highest enzyme activity as reference (100%). The various buffers were as follows;

1) Citric acid buffer (pH 5.0-6.0)
    2) Acetic acid-sodium acetate buffer (pH 4.0-6.0)
    3) MES buffer (pH 5.5-6.5)
    4) MOPS buffer (pH 6.5-7.5)
    5) Phosphate buffer (pH 6.0-8.0)
    6) Tris-HCl buffer (pH 7.0-9.0)
    7) Glycine-sodium hydroxide buffer (pH 8.5-10.5).

The results were shown in FIG. 3A; the optimal pH of HaHex74 was pH 6.5.

(2) Determination of pH Stability

HaHex74 was diluted with the above buffer, incubated at 35° C. for 30 min, rapidly cooled in ice water for 30 min, and then assayed for the enzyme activity. The relative enzyme activity of HaHex74 processed under different pH was calculated, taking the enzyme activity of untreated β-N-acetylhexosaminidase as reference (100%).

The results were shown in FIG. 3B: HaHex74 had good pH stability, and more than 80% enzyme activity remained after 30 min incubation at pH 5.5-9.0.

(3) Determination of Optimal Temperature

HaHex74 was appropriately diluted with 50 mM phosphate buffer (pH 6.5), and enzyme activity was measured at different temperatures (20, 25, 30, 35, 40, 45, 50, 55, 60, 65, 70° C.), respectively. The relative enzyme activity was calculated, taking the highest enzyme activity as reference (100%).

The results were shown in FIG. 3C; the optimal temperature of HaHex74 was 45° C.

(4) Determination of Thermostability

HaHex74 was appropriately diluted with 50 mM phosphate buffer (pH 6.5), incubated at different temperatures (20, 25, 30, 35, 40, 45, 50, 55, 60° C.) for 30 min, rapidly cooled in ice water for 30 min, and then assayed for enzyme activity. The relative enzyme activity of HaHex74 untreated under different pH was calculated, taking the enzyme activity of untreated β-N-acetylhexosaminidase as reference (100%).

The results were shown in FIG. 3D: HaHex74 had good stability below 45° C.

(4) Substrate Specificity

Colloidal chitin, ethylene glycol chitin, carboxymethyl cellulose (CMC), chitosan solution, p-nitrophenyl-β-N-acetylglucosaminide (pNP-GlcNAc) and p-nitrophenyl-β-N-acetylgalactosamine (pNP-GalNAc) were used as substrates for the determination of enzyme activity and investigation of substrate specificity under the standard enzyme activity assay conditions. The results were shown in Table 2.

TABLE 2

| Substrate specificity of the HaHex74 | | |
|---|---|---|
| Substrates | Specific enzyme activity (U mg$^{-1}$) | Relative activity (%) |
| pNP-GlcNAc | 385.3 ± 3.0 | 100 |
| pNP-GalNAc | 51.8 ± 1.8 | 13.4 |
| (GlcNAc)$_2$ | 73.4 ± 1.0$^a$ | 19.1 |

TABLE 2-continued

| Substrate specificity of the HaHex74 | | |
|---|---|---|
| Substrates | Specific enzyme activity (U mg$^{-1}$) | Relative activity (%) |
| (GlcNAc)$_3$ | 112.8 ± 2.2 | 29.3 |
| (GlcNAc)$_4$ | 54.3 ± 1.2 | 14.1 |
| (GlcNAc)$_5$ | 44.2 ± 2.3 | 11.5 |
| Colloidal chitin | 0.14 ± 0.06 | 0.04 |
| Ethylene glycol chitin | — | — |
| Chitosan | — | — |
| CMC | — | — |

Note:

$^a$method for measuring enzyme activity towards N-acetyl chitooligosaccharides: 0.1 mL of appropriately diluted enzyme solution was added to 0.1 mL of 1% (w/v, 10 g/L) N-acetyl chitooligosaccharides solution (prepared in 50 mM phosphate buffer, pH 6.5) and reacted at 45° C. for 10 min. The amount of β-N-acetylglucosamine released was determined by high-performance liquid chromatography (HPLC) with β-N-acetylglucosamine as a standard. HPLC conditions were: HPLC-RID detection system (Agilent 1260 infinity II, Agilent Technologies, USA) BP-800 Pb++ chromatography column (Benson Polymeric, Reno, NE, 7.8 × 300 mm, USA), distilled water as mobile phase, column temperature 80° C., flow rate 1 mL · min$^{-1}$. A standard enzyme-activity unit of β-N-acetylaminoglucosidase is given below: one unit (1 U) is the amount of enzyme required to produce 1 μmol of β-N-acetylglucosamine per minute under the above reaction conditions.

The results showed that: HaHex74 showed the highest activity (385.3 U/mg) towards pNP-GlcNAc; followed by N-acetyl chitotriose, N-acetyl chitobiose and N-acetyl chitotetraose. It showed weak activity towards colloidal chitin (0.14 U·mg$^{-1}$) and no activity towards glycol chitin, chitosan and CMC.

Example 3 Optimization of Conditions for the Synthesis of LNT2

The amount of synthesized LNT2 was determined by HPLC. HPLC assay conditions were: Waters XBridge BEH Amide 5 μm column (250×4.6 mm), 72% acetonitrile, column temperature 45° C., flow rate 0.5 mL/min, 45 min, differential refraction detector (RID).

Transglycosylation product yield (%)=concentration of synthesized product (mM)/initial concentration of glycoside donor (mM)×100

1. Determination of Optimal pH

The purified HaHex74 solution prepared in Example 2 was used as an enzyme solution to be detected and placed in different buffers respectively to determine a content of LNT2. The various buffers were as follows;

1) MES buffer (pH 5.5-6.5)
    2) Phosphate buffer (pH 6.0-8.0)
    3) Tris-HCl buffer (pH 7.0-9.0)

Figures 4A, 4B, 4C, 4D, 4E:
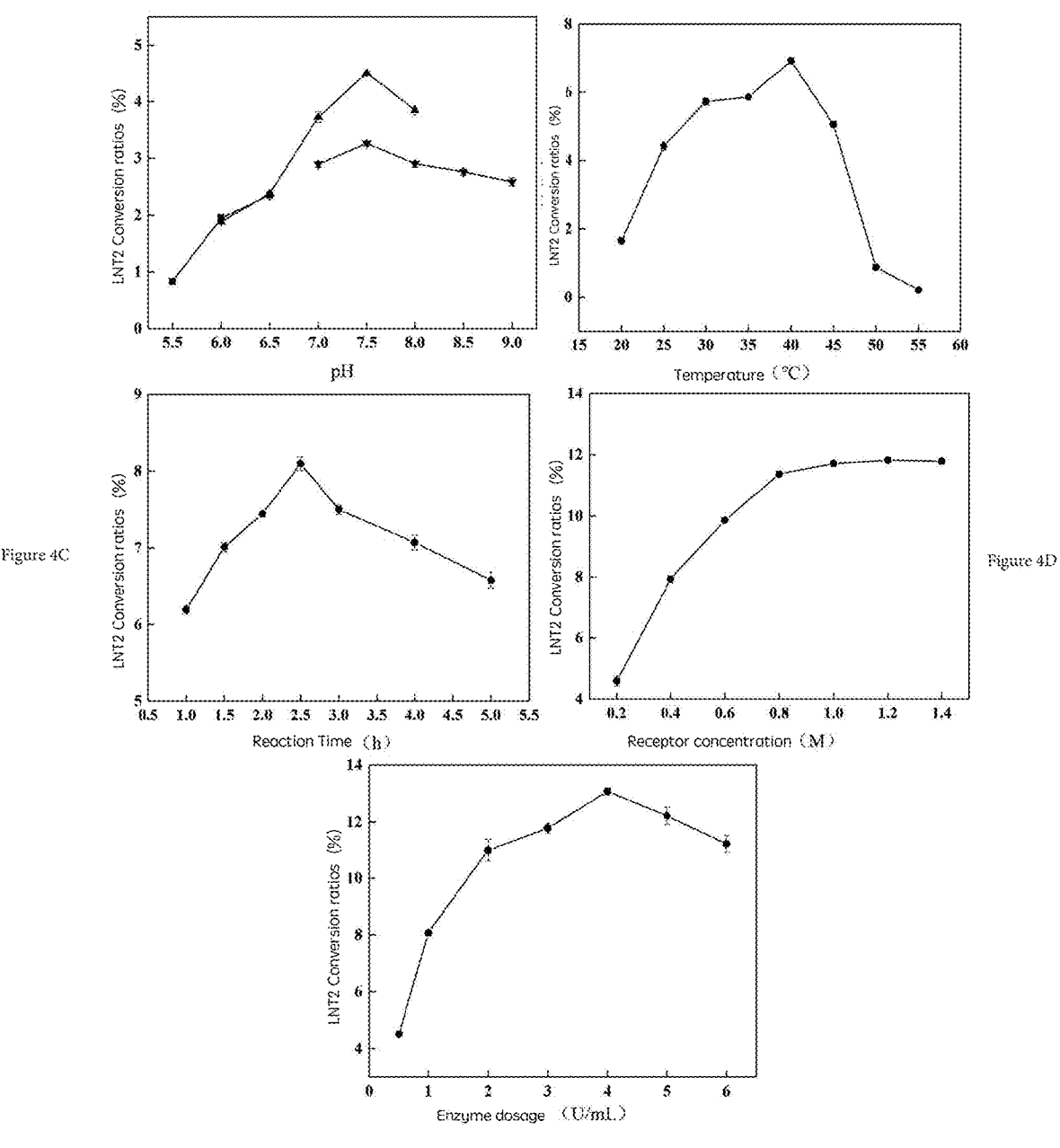
FIGS. 4A-4E Optimal pH (4A), optimal temperature (4B), optimal reaction time (4C), optimal β-lactose concentration (4D) and optimal enzyme dosage 4 (E) for the synthesis of LNT2 by HaHex74. Wherein, (■) MES buffer (pH 5.5-6.5), (▲) phosphate buffer (pH 6.0-8.0) and (▼) Tris-HCl buffer (pH 7.0-9.0).

The results were shown in FIG. 4A; the optimal pH for the synthesis of LNT2 by HaHex74 was pH 7.5.

2. Determination of Optimal Temperature

The purified HaHex74 solution prepared in Example 2 was used as an enzyme solution to be tested, and the reaction system was subjected to water bath reaction at different temperatures (20-55° C.) for 1.5 h to determine a content of LNT2.

The results were shown in FIG. 4B; the optimal temperature for the synthesis of LNT2 by HaHex74 was 40° C.

3. Determination of Optimal Reaction Time

The purified HaHex74 solution prepared in Example 2 was used as an enzyme solution to be detected, and the reaction system was subjected to a water bath reaction at 40° C. for different times to determine a content of LNT2. The results were shown in FIG. 4C; the optimal reaction time for the synthesis of LNT2 by HaHex74 was 2.5 h.

4. Determination of Optimal Concentration of Lactose

The purified HaHex74 solution prepared in Example 2 was used as an enzyme solution to be tested, the reaction system was added with different concentrations of β-lactose, and was subjected to water bath reaction at 40° C. for 2.5 h to Determine a Content of LNT2.

The results were shown in FIG. 4D; the optimal lactose concentration for the synthesis of LNT2 by HaHex74 was 0.8 M.

5. Determination of Optimal Enzyme Dosage

The purified HaHex74 solution prepared in Example 2 was used as an enzyme solution to be tested, the reaction system was added with different concentrations of HaHex74, and was subjected to water bath reaction at 40° C. for 2.5 h to determine a content of LNT2.

The results were shown in FIG. 4E; the optimal enzyme dosage for the synthesis of LNT2 by HaHex74 was 3-5 $U \cdot mL^{-1}$.

Example 4. Purification and Structural Identification of Synthesized LNT2

The product after the optimization of conditions in Example 3 was purified by HPLC. The collected product was subjected to TLC analysis for validation of purity (developing agent being n-butanol: ethanol: water=2:1:1 (v/v/v), and the color developer being methanol: sulfuric acid=95:5 (v/v)), and subjected to freeze drying to yield a white yellow powder sample.

The sample was dissolved in pure water and a high resolution primary mass spectrum of the sample was collected using a Thermo Scientific™ Q Exactive™ mass spectrometer in ESI ion source positive-ion mode.

The sample was dissolved in D20 and transferred to a nuclear magnetic dedicated tube, DSS (sodium 3-(trimethylsilyl)-1-propanesulfonate) was added as an internal standard, and the signal was collected at 298 K using a 500 MHz Varian V NMR SYSTEM™ instrument. All samples were analyzed for one-dimensional $^1H$ and $^{13}C$ spectra using an Agilent DD2 500 MHz NMR spectrometer, and for two-dimensional $^1H$-$^{13}C$ heteronuclear single quantum coherence spectroscopy (HSQC) using standard pulse sequences and related parameters provided by Agilent.

Figure 5:
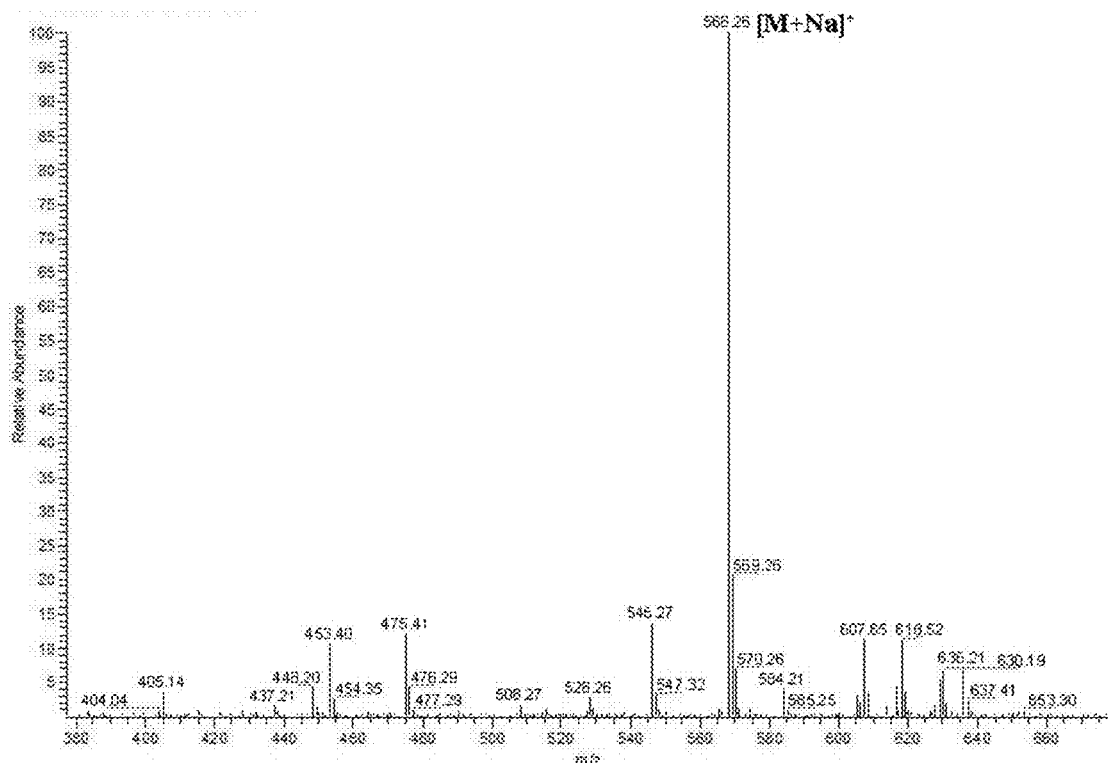
FIG. 5 MS spectrum of purified product synthesized by HaHex74.

The results showed that the purified product exhibited a single ion peak at a mass to charge ratio (m/z) $[M+Na]^+$ of 568.3 in the primary high-resolution mass spectrum (FIG. 5), indicating that the molecular weight of the product was 545.3, which was consistent with the molecular weight of LNT2 (545). Previous HPLC analysis of the HaHex74 synthesized product showed one major peak and one minor peak at the target product, which was shown to be an isomer by mass spectral analysis.

Figure 6:
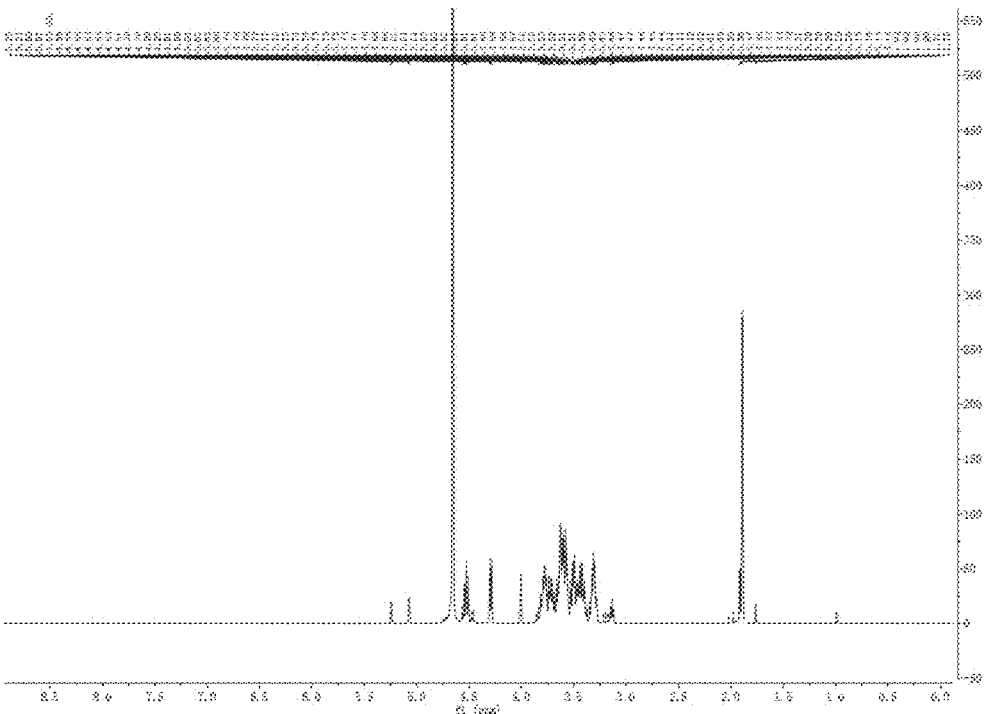
FIG. 6 ¹H spectrum of purified product synthesized by HaHex74.
Figure 7:
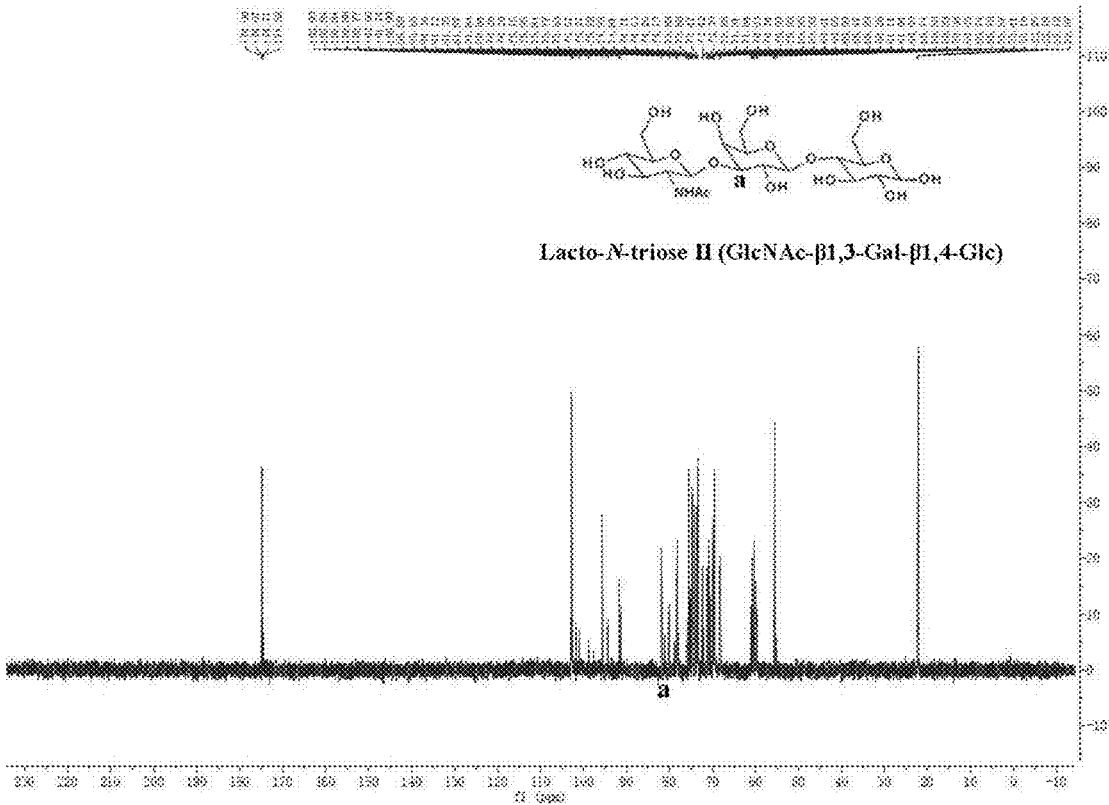
FIG. 7 ¹³C spectrum of purified product synthesized by HaHex74.
Figure 8:
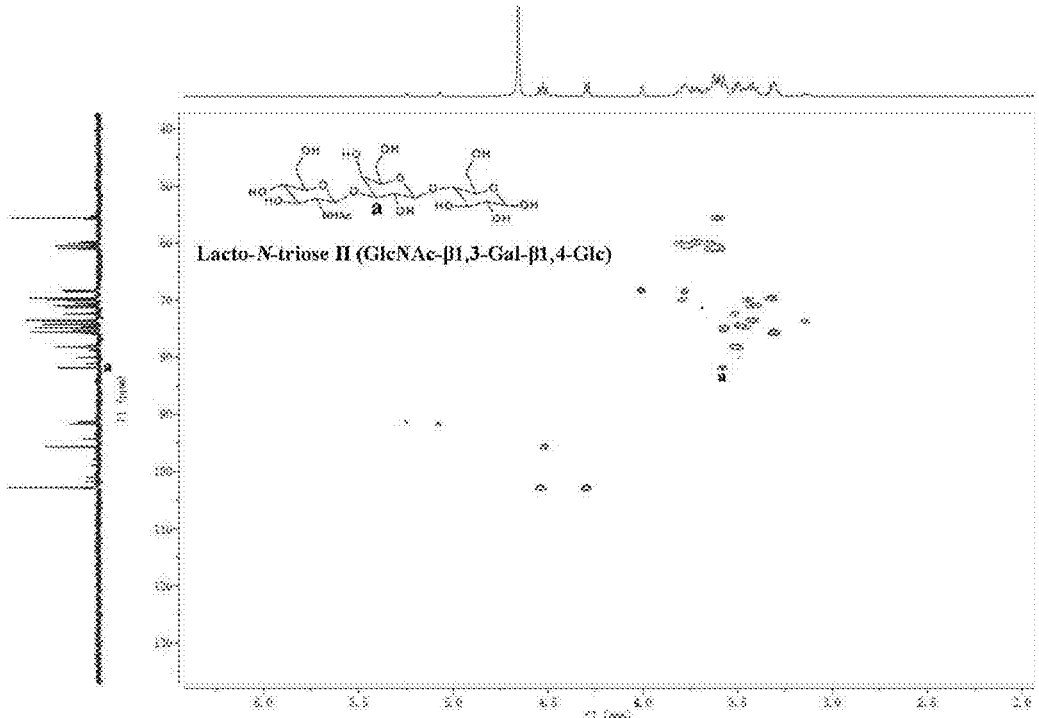
FIG. 8 Heteronuclear singular quantum correlation (HSQC) spectrum of purified product synthesized by HaHex74.

The structure of the transglycosylation product was further determined by NMR spectrum. $^1H$ chemical shift (FIG. 6) and $^{13}C$ chemical shift (FIG. 7) of the compound were obtained from the one-dimensional $^1H$ and $^{13}C$ spectra. The relationship between the carbon and hydrogen atoms of the compounds could be obtained from a two-dimensional heteronuclear single quantum coherence spectroscopy (HSQC) spectrum (FIG. 8). By data comparison, the HaHex74 product was consistent with the transglycosylation product of *Bifidobacterium bifidum*-derived β-N-acetylhexosaminidase mutant (Schmölzer et al. Glycosynthase principle transformed into biocatalytic process technology: Lacto-N-triose II production with engineered exo-hexosaminidase. ACS Catal. 2019, 9, 5503-5514), indicating that the compound is LNT2.

Example 5. LNT2 Production

1. Using Chitin as Starting Material 120 g of ball-milled chitin powder (3%, w/v) (Jiang Zhengqiang et al., ZL 201811105536.4) was dissolved in 4 L of 20 mM citric acid buffer (pH 5.5), 5 $U \cdot mL^{-1}$ of chitinase was added (Yang et al. Cloning, expression, purification and application of a novel chitinase from a thermophilic marine bacterium *Paenibacillus barengoltzii*. Food Chem., 2016, 192, 1041-1048), and hydrolyzed at 55° C. for 24 h.

2. Preparation of LNT2

The hydrolysate (a mixture of chitobiose and N-acetylglucosamine) obtained in step 1 was centrifuged, the supernatant was collected and concentrated by 10 times, $NaH_2PO_4$ was added to adjust the pH to 7.5, 0.8 M of β-lactose and 4 $U \cdot mL^{-1}$ HaHex74 (HaHex74 purified enzyme solution obtained in Example 2) were added, the mixture was reacted at 40° C., sampled at intervals, and content of LNT2 was determined by HPLC (see Example 3 for assay conditions).

LNT2 conversion ratio (%)=amount of synthesized LNT2 (M)/amount of chitobiose (M)×100%; wherein M represents the amount of a substance.

Figure 9:
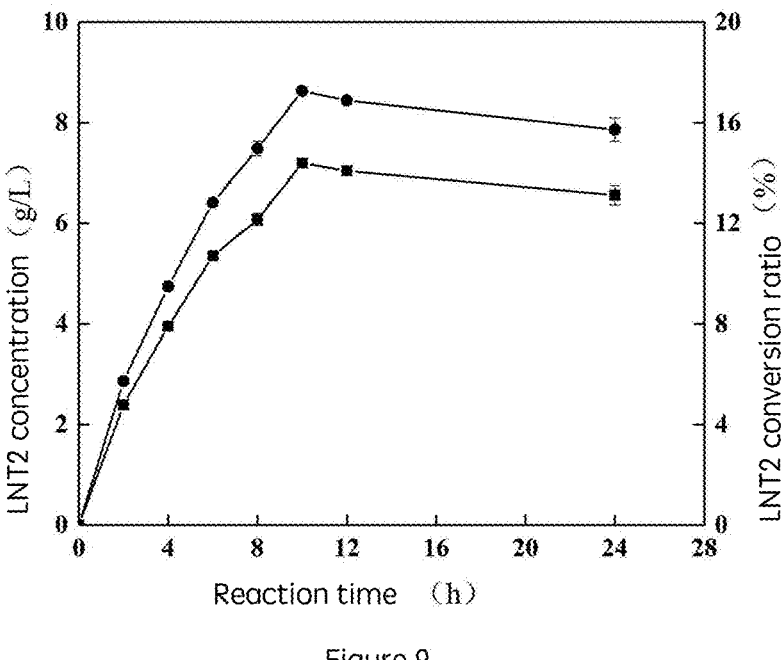
FIG. 9 Time course of LNT2 production using chitin hydeolysate and lactose by HaHex74 ((■): conversion ratio; (●): LNT2 concentration).

The results showed that the amount of LNT2 reached the maximum at 10 h with a conversion ratio of 13-20% and a concentration of 8-12 g· $L^{-1}$ (FIG. 9).

Example 6. LNnT production

The redundant β-lactose in the product of Example 5 described above was removed using an activated carbon column (75×1.5 cm), the product of Example 5 described above was subjected to gradient elution using a gradient mixer (TH-2000, Shanghai Qingpu Huxi Instrument Factory), and 0-25% (v/v) ethanol solution at a flow rate of 1 mL min-1, the eluent was collected and detected by TLC (see Example 4 for conditions) and HPLC (see Example 3 for conditions). The collected LNT2 solution was concentrated by 10 times with natural pH (pH 7.0) and 0.1 U $mL^{-1}$ of β-galactosidase was added (Zeuner et al. Thermostable β-galactosidases for the synthesis of human milk oligosaccharides. New Biotechnol., 2016, 33, 355-360), the mixture was reacted at 50° C. and sampled at intervals, all samples were inactivated in a boiling water bath for 10 min and subjected to HPLC analysis (see Example 3 for conditions).

LNnT conversion ratio (%)=amount of synthesized LNnT (M)/amount of lactose (M)×100%: wherein M represents the amount of a substance.

Figure 10:
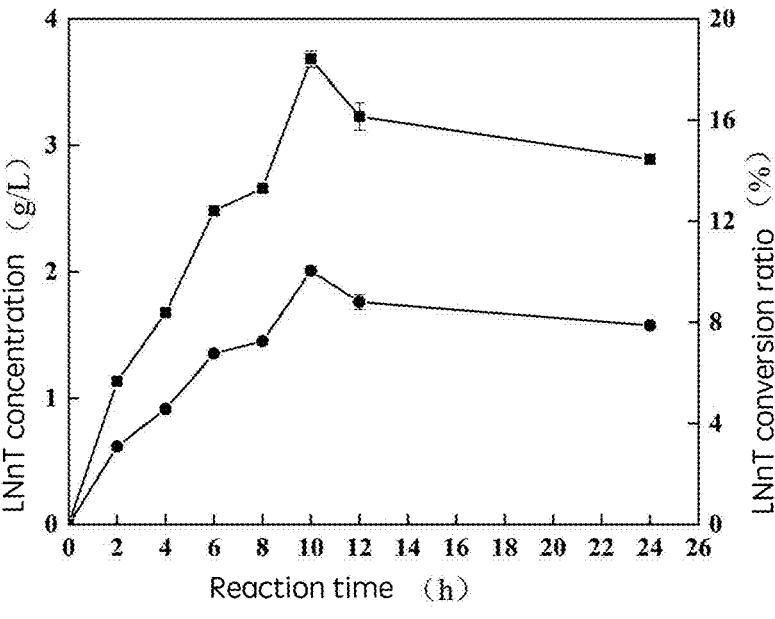
FIG. 10 Time course of LNnT production (((■): conversion ratio: (●): LNnT concentration).

The results showed that the collected LNT2 solution contained 20 mM β-lactose and 90 mM LNT2, and the reaction was conducted for 10 h, with the highest LNnT conversion ratio of 7-21%, and LNnT concentration of 1-3 g·$L^{-1}$ (FIG. 10).

The above are only preferred specific implementations of the present invention, but the protection scope of the present invention is not limited thereto. Any person skilled in the art can easily conceive modifications or replacements within the technical scope of the present invention, and these modifications or replacements shall fall within the protection scope of the present invention. Therefore, the protection scope of the present invention should be subject to the protection scope of the claims.

The content not described in detail in the specification belongs to the prior art known to those skilled in the art.

INDUSTRIAL APPLICATION

According to the invention, a glycoside hydrolase family 20 β-N-acetylhexosaminidase gene from *Haloferula* sp. (HaHex74) is efficiently expressed in *P. pastoris*. After high density fermentation in a 5-L fermentor, the enzyme activity of the fermentation broth can reach 3500 U·mL$^{-1}$, and the protein content is 9.7 g. L$^{-1}$, which is by far the highest expression level of β-N-acetylhexosaminidase. The newly invented β-N-acetylhexosaminidase HaHex74 displays excellent transglycosylation activity and can efficiently synthesize LNT2 (an important backbone precursor of human milk oligosaccharides) from natural donors chitobiose ((GlcNAc) 2) and β-lactose, with a conversion ratio of 10-20%, which is by far the highest level for the synthesis of LNT2 by β-N-acetylhexosaminidase using the natural donor. Powdery chitin can be efficiently converted into LNT2 by chitinase and HaHex74, and LNnT can be efficiently produced by further cooperating with a β-galactosidase, with LNT2 and LNnT concentrations of 8-12 g·L$^{-1}$ and 1-3 g·L$^{-1}$, respectively. The HaHex74 disclosed by the invention possesses high-level expression, excellent hydrolysis properties and transglycosylation activity, which may make it potentially useful in the production of human milk oligosaccharides.

---

The invention claimed is:

1. A method for the synthesis of Lacto-N-triose II, comprising one of (b1) or (b2) or (b3);

(b1) synthesizing Lacto-N-triose II (LNT2) from chitin hydrolysate and β-lactose under the catalysis of a HaHex74 protein as a biological enzyme under conditions comprising a pH of 7.5;

(b2) performing chitin hydrolysis catalyzed by a chitinase to obtain the chitin hydrolysate under conditions comprising a pH of 5.5; then synthesizing Lacto-N-triose II (LNT2) from the chitin hydrolysate and β-lactose under the catalysis of a HaHex74 protein under conditions comprising a pH of 7.5; or (b3) synthesizing Lacto-N-triose II (LNT2) from the chitin hydrolysate and β-lactose under the catalysis of the chitinase and HaHex74 protein as biological enzymes under conditions comprising a pH of 7.5;

wherein, the HaHex74 protein consists of at least one of the following proteins (A1), (A2), and (A3):

(A1) a protein consisting of an amino acid sequence at positions 94-745 of SEQ ID NO. 2 or shown in SEQ ID NO. 2;

(A2) a protein having an identity of at least 99% with the amino acid sequence defined in (A1) and having the same function and is derived from *Haloferula* sp.; and (A3) a fusion protein obtained by attaching a tag to the N-terminus and/or the C-terminus of the protein defined in any one of (A1) and (A2).

2. A method for the synthesis of Lacto-N-neotetraose comprising one of the following steps (c1) and (c2):

(c1) preparing Lacto-N-triose II (LNT2) according to the method of claim 1; then synthesizing Lacto-N-neotetraose (LNnT) from Lacto-N-triose II (LNT2) and β-lactose under the catalysis of a β-galactosidase; and (c2) synthesizing Lacto-N-triose II (LNT2) and Lacto-N-neotetraose (LNnT) from chitin and β-lactose under the catalysis of a chitinase, HaHex74 protein and β-galactosidase as biological enzymes, wherein the HaHex74 protein is any one of the following;

(A1) a protein consisting of an amino acid sequence at positions 94-745 of SEQ ID NO. 2 or shown in SEQ ID NO. 2;

(A2) a protein having 99% or more identity with the amino acid sequence defined in (A1) and having the same function which is derived from *Haloferula* sp.; and (A3) a fusion protein obtained by attaching a tag to the N-terminus and/or the C-terminus of the protein defined in any one of (A1) and (A2).

3. The method according to claim 1, wherein, in the step (b1) or the step (b2), the chitin hydrolysate consists of a mixture of N-acetyl chitobiose and N-acetylglucosamine.

4. The method according to claim 1, wherein, Lacto-N-triose II (LNT2) is synthesized from chitin hydrolysate and β-lactose under catalysis at a catalysis temperature of 40° C., and/or a content of β-lactose in a reaction system of 0.8 M; and/or a content of the HaHex74 protein in the reaction system of 3-5 U/mL, and/or a reaction time of 10 h.

5. The method according to claim 1, wherein, chitin hydrolysate is obtained from the hydrolysis of chitin by the chitinase under conditions comprising a catalysis temperature of 55° C., and/or a content of the chitinase in a reaction system of 5 U/mL, and/or a reaction time of 24 h.

6. The method according to claim 1, wherein, Lacto-N-neotetraose (LNnT) is synthesized from Lacto-N-triose II (LNT2) and β-lactose by a β-galactosidase under conditions of natural pH (pH 7.0), and/or a temperature of 50° C., and/or a content of β-galactosidase in a reaction system of 0.1 U/mL, and/or a reaction time of 10 h.

7. The method according to claim 1, wherein, the HaHex74 protein is prepared according to a method comprising the steps;

introducing a nucleic acid molecule encoding the HaHex74 protein into a yeast receptor to obtain recombinant yeast;

performing fermentation culture on the recombinant yeast according to the following steps and Pichia Fermentation Process Guidelines to obtain the HaHex74 protein from a fermentation product;

(d1) a basic culture stage: inoculating the recombinant yeast into BSM medium supplemented with 50 g/L glycerol for culture, adjusting a temperature to 30° C. and pH to 4.0, and starting the glycerol fed-batch culture stage when the glycerol concentration is below 10 g/L;

(d2) a glycerol fed-batch culture stage: feeding 500 g/L glycerol, maintaining the glycerol concentration at 10-25 g/L, adjusting a temperature to 28° C., pH to 5.0, and maintaining the dissolved oxygen content to 10-20% until the end of fermentation.

8. The method according to claim 7, wherein, obtaining the HaHex74 protein from the fermentation product is performed according to a process comprising the steps of centrifuging the fermentation product to collect supernatant; dialyzing the supernatant in a Tris-HCl buffer solution, and centrifuging to obtain crude enzyme; followed by purifying the crude enzyme using a (diethylamino) ethyl DE52 column (DEAE Sepharose Fast Flow) to obtain the HaHex74 protein.

9. The method according to claim 7, wherein, the nucleic acid molecule encoding the HaHex74 protein is a DNA molecule as described in any one of the following;

(B1) a DNA molecule represented by positions 280-2238 of SEQ ID NO. 3 or SEQ ID NO. 3;

(B2) a DNA molecule having 99% or more, 95% or more, 90% or more, 85% or more or 80% or more identity with the DNA sequence defined by (B1) and encoding the HaHex74 protein.

10. The method according to claim 7, wherein, the nucleic acid molecule is introduced into the yeast receptor in the form of a recombinant vector; wherein, the promoter in the recombinant vector that initiates transcription of the nucleic acid molecule is a glyceraldehyde-3-phosphate dehydrogenase (GAP) promoter.

11. The method according to claim 10, wherein, the sequence of the GAP promoter is shown in SEQ ID NO. 1.

12. The method according to claim 7, wherein, the yeast is *Pichia pastoris*.

13. The method according to claim 12, wherein the *Pichia pastoris* is *Pichia pastoris* GS115.

14. A preparation method of HaHex74 protein, comprising the following steps: introducing a nucleic acid molecule encoding the HaHex74 protein into a yeast receptor to obtain recombinant yeast; performing fermentation culture on the recombinant yeast according to the following steps and Pichia Fermentation Process Guidelines to obtain the HaHex74 protein from a fermentation product;

(d1) a basic culture stage: inoculating the recombinant yeast into BSM medium supplemented with 50 g/L glycerol for culture, adjusting the temperature to 30° C. and pH to 4.0, and starting the glycerol fed-batch culture stage when the glycerol concentration is below 10 g/L, (d2) a glycerol fed-batch culture stage: feeding 500 g/L glycerol, maintaining the glycerol concentration to 10-25 g/L, adjusting a temperature to 28° C., pH to 5.0, and maintaining the dissolved oxygen content to 10-20% until the end of fermentation;

the HaHex74 protein is any one of the following;

(A1) a protein consisting of an amino acid sequence at positions 94-745 of SEQ ID NO. 2 or shown in SEQ ID NO. 2;

(A2) a protein having 99% or more identity with the amino acid sequence defined in (A1) and having the same function and is derived from Haloferul a sp.; and (A3) a fusion protein obtained by attaching a tag to the N-terminus and/or the C-terminus of the protein defined in any one of (A1) and (A2).

15. The preparation method according to claim 14, wherein, obtaining the HaHex74 protein from the fermentation product is performed according to a process comprising the steps of centrifuging the fermentation product to collect supernatant; dialyzing the supernatant in a Tris-HCl buffer solution, and centrifuging to obtain crude enzyme; followed by purifying the crude enzyme using a (diethylamino) ethyl DE52 column (DEAE Sepharose Fast Flow) to obtain the HaHex74 protein.

16. The preparation method according to claim 14, wherein, the nucleic acid molecule encoding the HaHex74 protein is a DNA molecule as described in any one of the following;

(B1) a DNA molecule at positions 280-2238 of SEQ ID NO. 3 or SEQ ID NO. 3;

(B2) a DNA molecule having 99% or more identity with the DNA sequence defined by (B1) and encoding the HaHex74 protein.

17. The preparation method according to claim 14, wherein, the nucleic acid molecule is introduced into the yeast receptor in the form of a recombinant vector; wherein, the promoter in the recombinant vector that initiates transcription of the nucleic acid molecule is a GAP promoter.

18. The preparation method according to claim 17, wherein, the sequence of the GAP promoter is shown in SEQ ID NO. 1.

19. The preparation method according to claim 14, wherein, the yeast is *Pichia pastoris*.

20. The preparation method according to claim 19, wherein the *Pichia pastoris* is *Pichia pastoris* GS115.

\* \* \* \* \*